United States Patent
Matsumoto

(10) Patent No.: US 9,435,750 B2
(45) Date of Patent: Sep. 6, 2016

(54) BORESCOPE

(71) Applicant: HONDA MOTOR CO., LTD., Tokyo (JP)

(72) Inventor: Kenji Matsumoto, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 14 days.

(21) Appl. No.: 14/011,759

(22) Filed: Aug. 28, 2013

(65) Prior Publication Data

US 2014/0071444 A1  Mar. 13, 2014

(30) Foreign Application Priority Data

Sep. 12, 2012 (JP) ................................ 2012-200164

(51) Int. Cl.
| | |
|---|---|
| *G01N 21/00* | (2006.01) |
| *G01N 21/954* | (2006.01) |
| *G02B 23/24* | (2006.01) |

(52) U.S. Cl.
CPC ......... *G01N 21/954* (2013.01); *G02B 23/2446* (2013.01); *G02B 23/2484* (2013.01)

(58) Field of Classification Search
CPC ...... B23K 26/08; B23K 26/06; G02B 13/00; G02B 17/08; G02B 15/22; G02B 13/0095; H01L 21/027; G03F 7/20; G03B 17/14
USPC ................ 356/241.1; 385/117, 118; 359/725
See application file for complete search history.

(56) References Cited

U.S. PATENT DOCUMENTS

| | | | | |
|---|---|---|---|---|
| 2,975,785 A | * | 3/1961 | Sheldon ......................... | 600/141 |
| 3,694,094 A | * | 9/1972 | Low et al. ................. | 356/241.4 |
| 4,230,403 A | * | 10/1980 | Hashimoto et al. .......... | 396/298 |
| 4,317,627 A | * | 3/1982 | Isobe et al. .................... | 396/530 |
| 4,580,886 A | * | 4/1986 | Hajnal .................... | G02B 23/08 348/335 |
| 4,868,588 A | * | 9/1989 | Hajnal .................... | G02B 23/08 352/94 |
| 5,430,575 A | * | 7/1995 | Sudarshan ............. | G02B 17/02 359/434 |
| 5,469,236 A | * | 11/1995 | Roessel .................. | G02B 23/08 352/94 |

(Continued)

FOREIGN PATENT DOCUMENTS

| | | |
|---|---|---|
| DE | 1900017 | 8/1970 |
| GB | 2040064 | 8/1980 |

(Continued)

OTHER PUBLICATIONS

Japanese Office Action for corresponding JP Application No. 2012-200164, Nov. 25, 2015.

*Primary Examiner* — Tarifur Chowdhury
*Assistant Examiner* — Isiaka Akanbi
(74) *Attorney, Agent, or Firm* — Mori & Ward, LLP

(57) ABSTRACT

A borescope includes a plurality of bending parts, a plurality of lens barrels, a plurality of joint parts, an objective lens device, a plurality of reflectors, a plurality of relay lenses, and a camera mount. The plurality of lens barrels are connected via the plurality of bending parts with predetermined bend angles, respectively. Rotation angles of the plurality of bending parts are changeable via the plurality of joint parts relative to the plurality of lens barrels. The objective lens device has an objective lens and is detachably provided at a front end side of the plurality of lens barrels. The plurality of reflectors are respectively disposed in the plurality of bending parts. The plurality of relay lenses are respectively disposed in the plurality of lens barrels. The camera mount is provided at a rear end side of the plurality of lens barrels.

19 Claims, 13 Drawing Sheets

(56) References Cited

U.S. PATENT DOCUMENTS

| | | | |
|---|---|---|---|
| 5,694,628 A * | 12/1997 | Nishitani | 396/379 |
| 8,446,681 B2 * | 5/2013 | Terada | 359/817 |
| 2003/0128973 A1 * | 7/2003 | Shinohara et al. | 396/25 |
| 2005/0057822 A1 * | 3/2005 | Hayashi | 359/694 |
| 2009/0237810 A1 * | 9/2009 | Frazier et al. | 359/744 |

FOREIGN PATENT DOCUMENTS

| | | |
|---|---|---|
| JP | 55-153913 | 12/1980 |
| JP | 57-124323 | 8/1982 |
| JP | 63-281121 | 11/1988 |
| JP | 05-72618 | 3/1993 |
| JP | 05-072618 | 3/1993 |
| JP | 3150206 B2 | 9/1993 |
| JP | 06-051235 | 2/1994 |
| JP | 10-020628 | 1/1998 |
| JP | 2001-503159 | 3/2001 |
| JP | 2003-207419 | 7/2003 |
| JP | 3786658 B2 | 7/2005 |
| WO | WO 2004/073052 | 8/2004 |

* cited by examiner

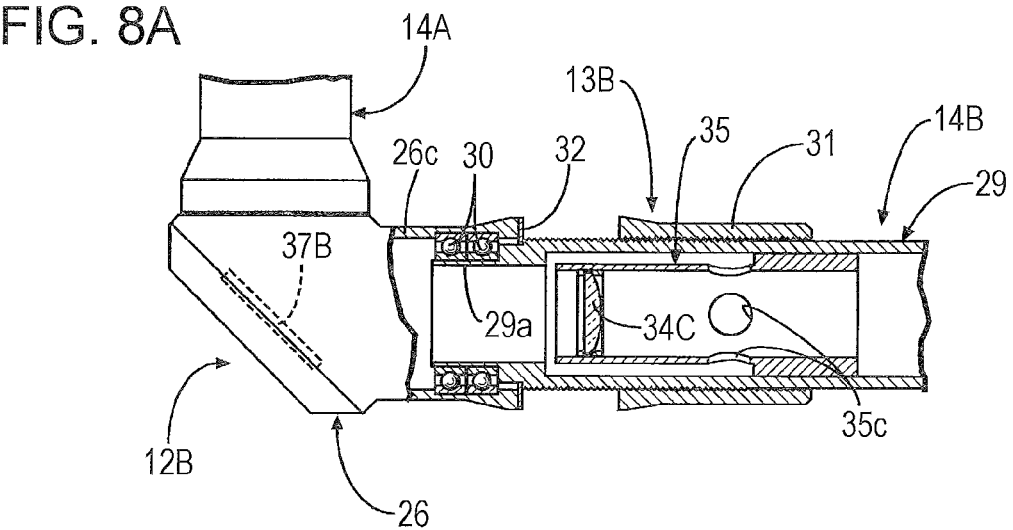
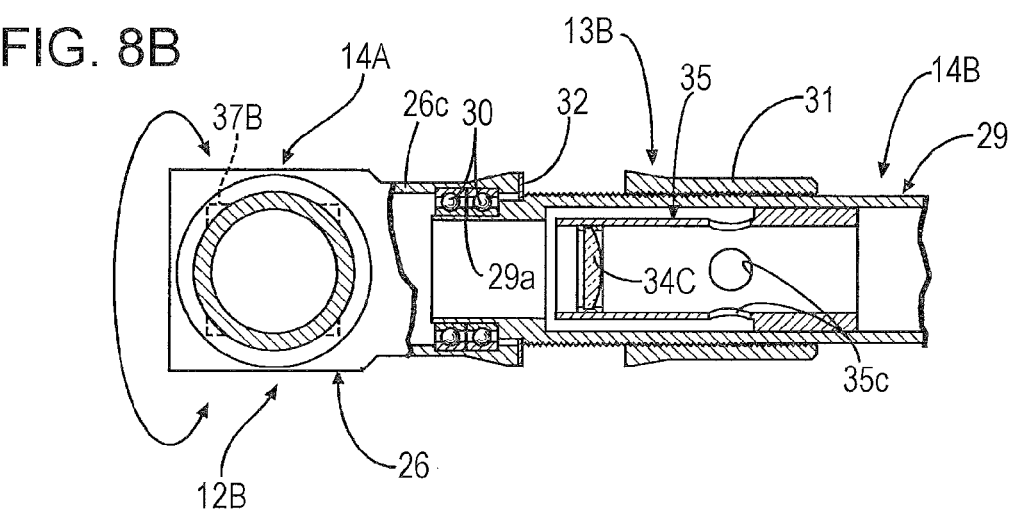
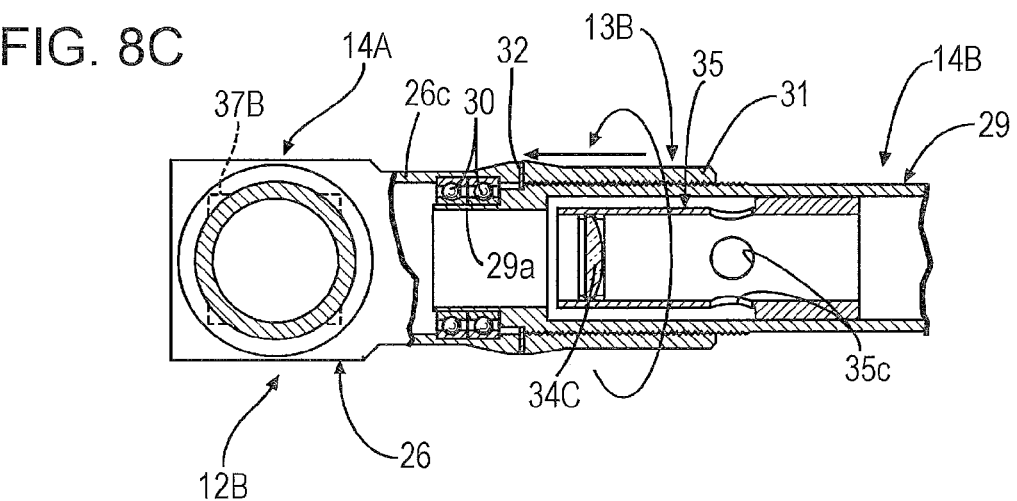

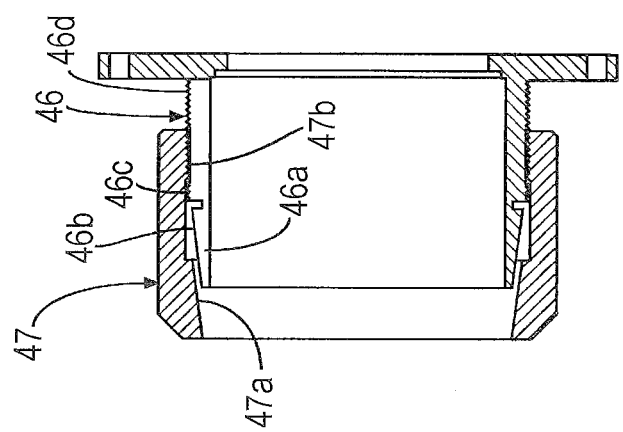
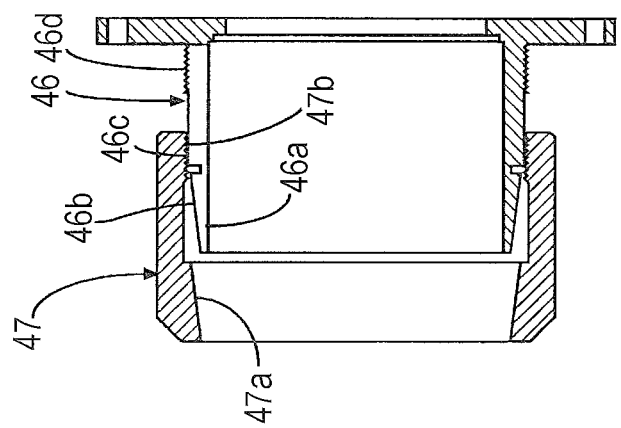
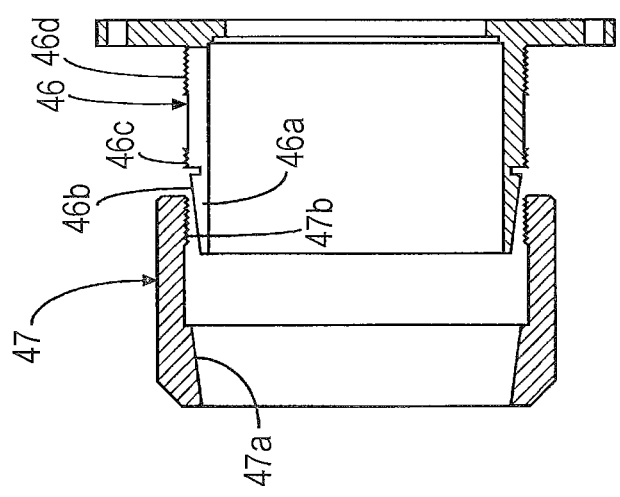

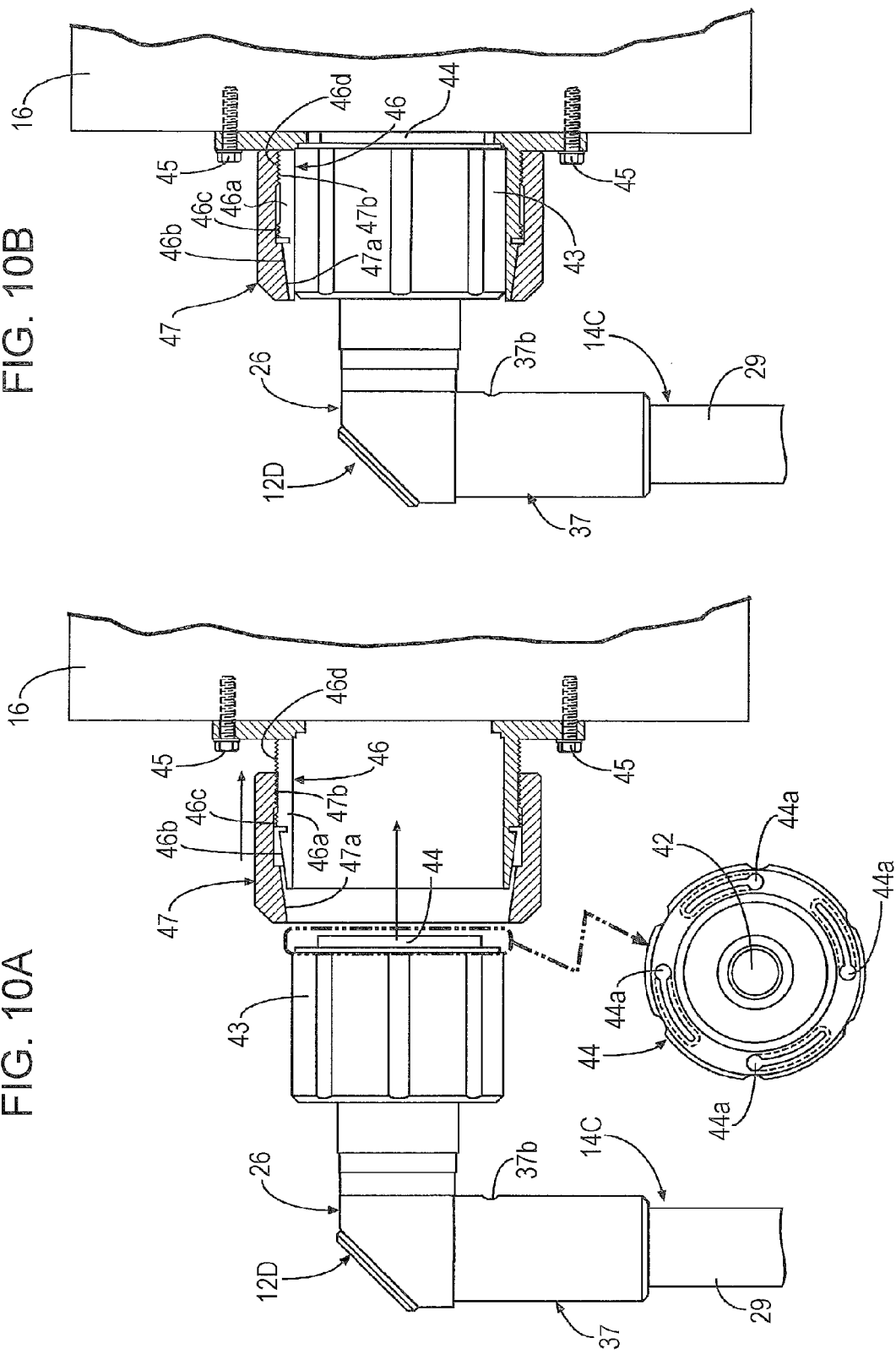

BORESCOPE

CROSS-REFERENCE TO RELATED APPLICATIONS

The present application claims priority under 35 U.S.C. §119 to Japanese Patent Application No. 2012-200164, filed Sep. 12, 2012, entitled "Borescope." The contents of this application are incorporated herein by reference in their entirety.

BACKGROUND OF THE INVENTION

1. Field of the Invention

The present disclosure relates to a borescope.

2. Discussion of the Background

An optical system for long distance transmission is publicly known from Japanese Patent No. 3786658. The optical system allows a laser beam to be transmitted to an object to be processed via a relay lens, a collimator lens, a plurality of galvanomirrors, and a condensing lens, the laser beam being emitted from a laser beam source.

A borescope is publicly known from Japanese Patent No. 3150206, in which an objective probe is swingably connected to the front end of an eyepiece assembly, the front end being capable of bending like a crank, and light from a light source is transmitted to the rear end of the objective probe via an optical guide cable, and thus an object can be irradiated with the light.

SUMMARY OF THE INVENTION

According to one aspect of the present invention, a borescope includes a plurality of bending parts, a plurality of lens barrels, a plurality of joint parts, an objective lens device, a plurality of reflectors, a plurality of relay lenses, and a camera mount. The plurality of lens barrels are connected via the plurality of bending parts with predetermined bend angles, respectively. Rotation angles of the plurality of bending parts are changeable via the plurality of joint parts relative to the plurality of lens barrels. The objective lens device has an objective lens and is detachably provided at a front end side of the plurality of lens barrels. The plurality of reflectors are respectively disposed in the plurality of bending parts. The plurality of relay lenses are respectively disposed in the plurality of lens barrels. The camera mount is provided at a rear end side of the plurality of lens barrels.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIGS. 8A to 8C are operation explanatory views of a joint according to the first embodiment.

FIGS. 9A to 9C are a first set of operation explanatory views of a camera mount according to the first embodiment.

FIGS. 10A and 10B are a second set of operation explanatory views of the camera mount according to the first embodiment.

DESCRIPTION OF THE EMBODIMENTS

Figure 1:
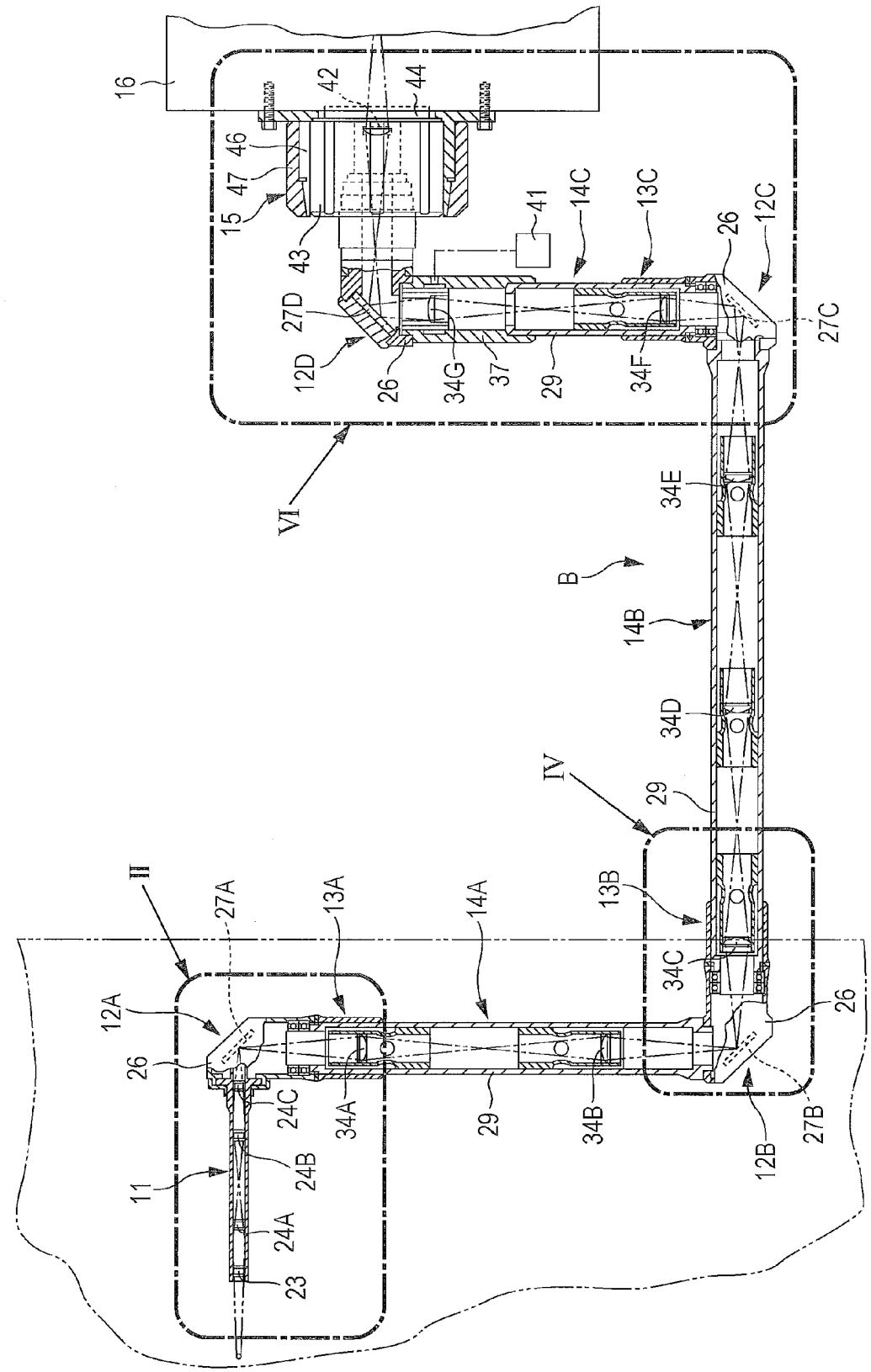
FIG. 1 is a front view of a borescope according to a first embodiment.

The embodiments will now be described with reference to the accompanying drawings, wherein like reference numerals designate corresponding or identical elements throughout the various drawings.

First Embodiment

Hereinafter, a first embodiment of the present disclosure will be described with reference to FIGS. 1 to 10B. It is to be noted that a direction toward an objective lens 23 is defined as a forward direction, and a direction toward an eyepiece lens 42 side is defined as a rearward direction.

When the temperature, for example, in the engine or transmission of an automobile is measured in a non-contact manner, the object to be measured from the outside is captured by a borescope B. As illustrated in FIG. 1, the borescope B is formed by successively connecting an objective lens unit 11, a first bending part 12A, a first joint part 13A, a first lens barrel 14A, a second bending part 12B, a second joint part 13B, a second lens barrel 14B, a third bending part 12C, a third joint part 13C, a third lens barrel 14C, a fourth bending part 12D, and a camera mount 15 from a forward to rearward. A camera 16 is detachably connected to the camera mount 15.

The objective lens unit 11 and the first lens barrel 14A are connected via the first bending part 12A with a bend angle of 90°; the first lens barrel 14A and the second lens barrel 14B are connected via the second bending part 12B with a bend angle of 90°; the second lens barrel 14B and the third lens barrel 14C are connected via the third bending part 12C with a bend angle of 90°; and the third lens barrel 14C and the camera mount 15 are connected via the fourth bending part 12D with a bend angle of 90°. The first bending part 12A and the first lens barrel 14A are relatively rotatable via the first joint part 13A for any rotational angle; The second bending part 12B and the second lens barrel 14B are relatively rotatable via the second joint part 13B for any rotational angle; and the third bending part 12C and the third lens barrel 14C are relatively rotatable via the third joint part 13C for any rotational angle. Consequently, the relative position and the relative angle of the objective lens unit 11 with respect to the camera 16 can be changed with a significant degree of freedom.

Figure 2:
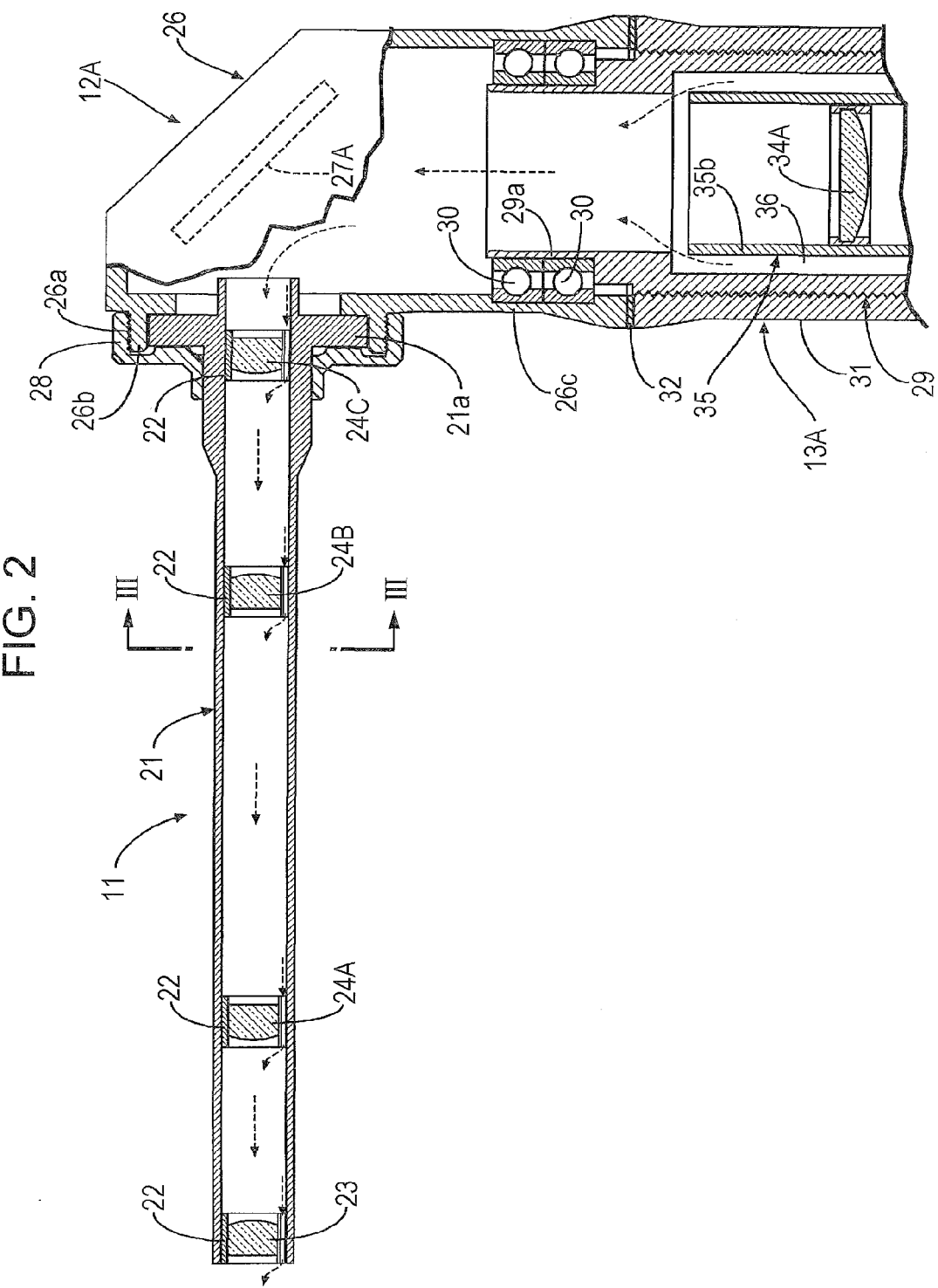
FIG. 2 is an enlarged view of portion II of FIG. 1.

As illustrated in FIG. 2, the object lens unit 11 includes a linear pipe member 21 with a flange 21a at the rear end. The objective lens 23 is supported via a lens holder 22 at the front end of the pipe member 21, and first to third relay lenses 24A, 24B, and 24C are supported rearwardly of the objective lens 23 via three lens holders 22, 22, and 22, respectively.

Figure 3:
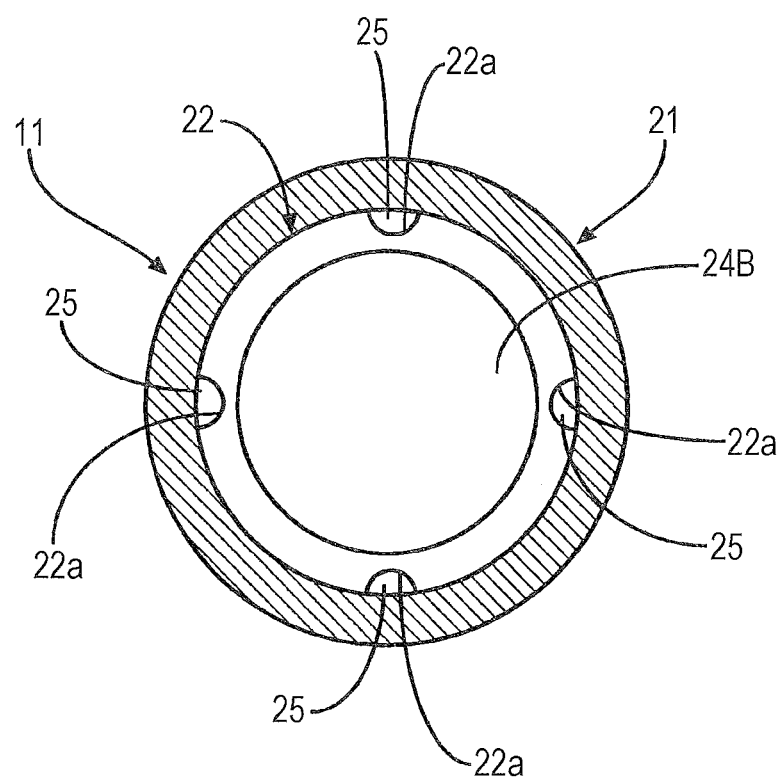
FIG. 3 is a cross-sectional view taken along line III-III of FIG. 2.

As illustrated in FIG. 3, the cylindrical four lens holders 22, ... which internally support the objective lens 23 and the first to third relay lenses 24A, 24B, 24C, have the same structure, and include four respective grooves 22a, ... which extend axially on the outer circumferential surface. Air passages 25, ... through which air can flow, are formed between the grooves 22a, ... and the inner circumferential surface of the pipe member 21. It is to be noted that the air passage 25 of the lens holder 22 of the objective lens 23 serves as an air discharge hole 25' for discharging air to the outside of the borescope B.

As illustrated in FIG. 2, the first bending part 12A includes a housing 26, and a first mirror 27A is mounted in the housing 26. The first mirror 27A intersects both the axis of the objective lens unit 11 and the axis of the first lens barrel 14A with an angle of 45°. An annular projection 26b having a male screw 26a on its outer circumference is formed on the end face of the housing 26 near the objective lens unit 11. A fixed ring 28 is screwed onto the male screw 26a of the outer circumference of the projection 26b with the flange 21a of the pipe member 21 of the objective lens unit 11 being inserted in the annular projection 26b, and thus the objective lens unit 11 is detachably fixed to the first bending part 12A.

Figure 4:
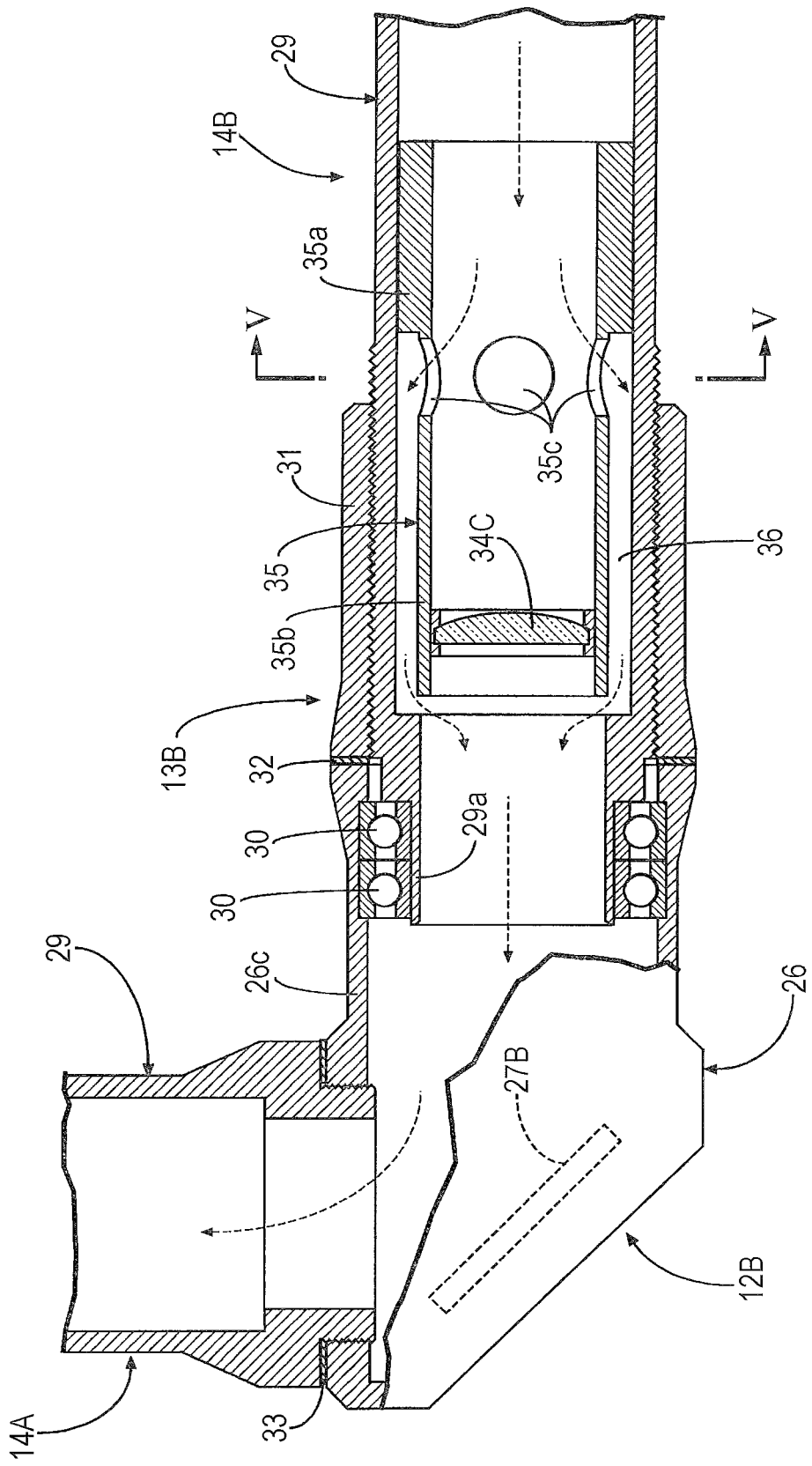
FIG. 4 is an enlarged view of portion IV of FIG. 1.
Figure 5:
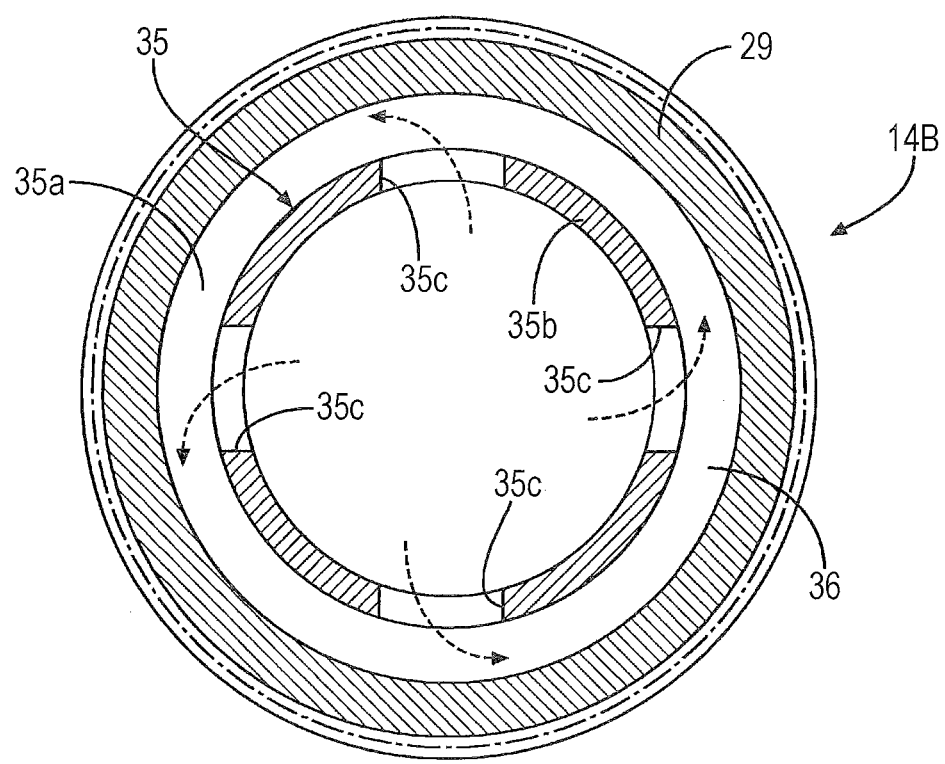
FIG. 5 is a cross-sectional view taken along line V-V of FIG. 4.

As illustrated in FIG. 4, the second joint part 13B includes an inner cylindrical portion 29a which is formed integrally with the front end of a linear pipe member 29 included in the second lens barrel 14B, an outer cylindrical portion 26c which is formed integrally with the housing 26 of the second bending part 12B and fits into the outer circumference of the inner cylindrical portion 29a, two ball bearings 30, 30 (bearing) disposed between the inner cylindrical portion 29a and the outer cylindrical portion 26c, a lock ring 31 which is screwed into the outer circumference of the pipe member 29, and an annular friction material 32 which is sandwiched between the opposed end faces of the outer cylindrical portion 26c and the lock ring 31. The housing 26 of the second bending part 12B is threadedly connected to the rear end of the pipe member 29 of the first lens barrel 14A with a sealing member 33 interposed.

The structure of the first joint part 13A and the third joint part 13C is the same as the structure of the above-described second joint part 13B, and thus redundant description thereof is omitted.

As illustrated in FIG. 1, fourth and fifth relay lenses 34A, 34B are supported in the first lens barrel 14A, sixth to eighth relay lenses 34C, 34D, 34E are supported in the second lens barrel 14B, and ninth and tenth relay lenses 34F, 34G are supported in the third lens barrel 14C via respective lens holders 35. The fourth to ninth relay lenses 34A to 34F are the lens holders 35, . . . , 38 are the same, and one of them will be described as a representative with reference to FIGS. 4 and 5. The cylindrical lens holder 35 includes a large diameter portion 35a and a small diameter portion 35b. The large diameter portion 35a is fixed to the inner circumferential surface of the pipe member 29 of the second lens barrel 14B, and the sixth relay lens 34C is fixed to the inner circumferential surface of the small diameter portion 35b. Four air holes 35c, ... are open in the small diameter portion 35b adjacent to the large diameter 35a, and communicate with an air passage 36 which is between the inner circumferential surface of the pipe member 29 and the outer circumferential surface of the small diameter portion 35b.

Figure 6:
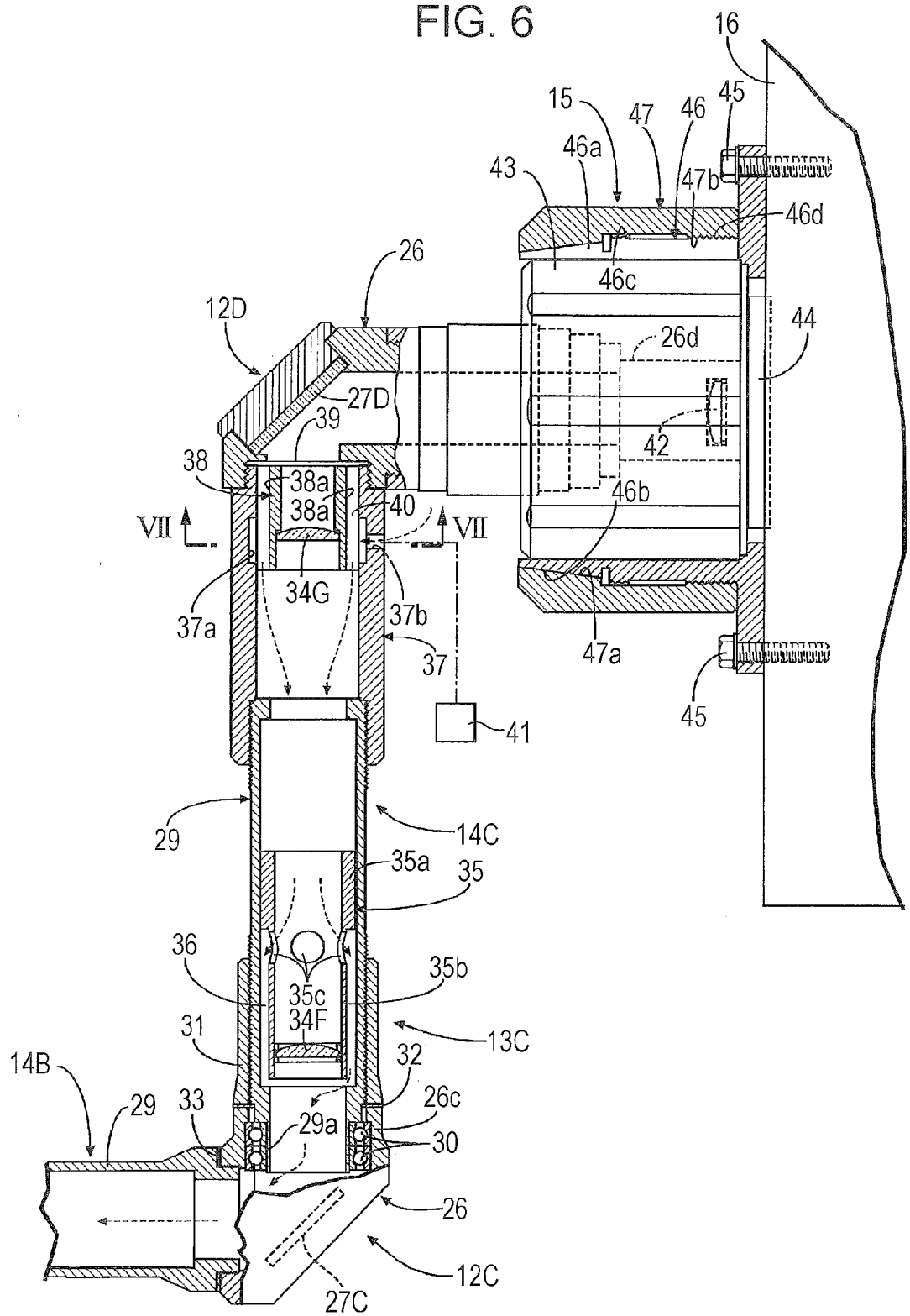
FIG. 6 is an enlarged view of portion VI of FIG. 1.

Unlike the above-described first lens barrel 14A and the second lens barrel 14B, the third lens barrel 14C includes the pipe member 29 on the front side and a pipe member 37 on the rear side which are connected in series as illustrated in FIGS. 6 and V. The pipe member 29 on the front side is the same as the pipe members 29, 29 of the first lens barrel 14A and the second lens barrel 14B. The front end of the pipe member 37 on the rear side is screwed into the pipe member 29 on the front side, and the rear end of the pipe member 37 on the rear side is screwed into the housing 26 of the fourth bending part 12D.

The lens holder 38, which holds the tenth relay lens 34G at the pipe member 37 on the rear side, has a different shape from that of the lens holders 35, . . . which hold the fourth to ninth relay lenses 34A to 34F. That is to say, the rear end of the lens holder 38 that is fixed to the inside of the pipe member 37 is in contact with a transparent partition plate 39 and closed, the partition plate 39 being sandwiched between the pipe member 37 and the housing 26 of the fourth bending part 12D. An annular groove 37a, which is formed in the inner circumferential surface of the pipe member 37, communicates with four grooves 38a, . . . which are axially formed in the outer circumferential surface of the lens holder 38, thereby forming air passages 40, . . . . The annular groove 37a is connected to an air supply source 41 via an air supply hole 37b which penetrates the pipe member 37.

The inside of a camera connecting portion 26d at the rear end of the housing 26 of the fourth bending part 12D is provided with the eyepiece lens 42, and a zoom housing 43 fits into the outer circumference of the eyepiece lens 42. The rear end of the camera connecting portion 26d is provided with a bayonet auxiliary camera mount 44 (see FIGS. 10A and 10B), and a commercial digital camera (not illustrated) can be detachably attached to any of bayonet grooves 44a, . . . of the auxiliary camera mount 44.

As illustrated in FIGS. 6, 9A to 9C, the camera mount 15, to which the camera 16 can be detachably attached, includes a spring collet 46 which is fixed to the camera 16 via bolts 45, . . . , and a fixed ring 47 which is threadedly connected to the outer circumference of the spring collet 46. The spring collet 46 includes four slits 46a, . . . which extend in the axial direction with an interval of 90°, an outer circumferential tapered surface 46b which is formed on the front end side of the slits 46a, . . . , a first male screw 46c which is formed rearwardly of the outer circumferential tapered surface 46b, and a second male screw 46d which is formed further rearwardly of the first male screw 46c. On the other hand, the fixed ring 47 includes an inner circumferential tapered surface 47a which is formed on the front end side, and a female screw 47b which is formed on the rear end side.

The outer circumferential tapered surface 46b of the spring collet 46 can be in contact with the inner circumferential tapered surface 47a of the fixed ring 47, and the female screw 47b of the fixed ring 47 can be screwed into the first male screw 46c and the second male screw 46d of the spring collet 46.

In the following, the operation of the first embodiment with the aforementioned configuration of the present disclosure will be described.

First, the rotation angles of the first joint part 13A to the third joint part 13C of the borescope B are adjusted according to a subject having a temperature to be measured.

Because the operations of the first joint part 13A to the third joint part 13C are the same, the case of the second joint part 13B will be described. As illustrated in FIG. 8A, the lock ring 31 is loosened to relieve the pressure which is applied to the friction material 32, and then the pipe member 29 and the housing 26 are relatively rotated via the ball bearings 30, 30 as illustrated in FIG. 8B so as to establish a predetermined positional relationship. When the lock ring 31 is tightened to compress the friction material 32 in the above state, the second bending part 12B and the second lens barrel 14B are integrated by a frictional force as illustrated in FIG. 8C. Thus, by adjusting the rotation angles of the first joint part 13A to the third joint part 13C, the objective lens unit 11 can be inserted into a narrow inside of the engine or transmission so as to face an object to be measured.

The operation of mounting the camera 16 on the camera mount 15 is performed by the procedure illustrated in FIGS. 9A to 9C, 10A, and 10B. As illustrated in FIGS. 9A and 9B, the female screw 47b of the fixed ring 47 is previously screwed into the first male screw 46c of the spring collet 46, and as illustrated in FIG. 9C, the female screw 47b is stopped at the position where the female screw 47b has just passed the first male screw 46c. In the above state, the female screw 47b is not screwed into the first male screw 46c or the second male screw 46d. However, the female screw 47b interferes with the first male screw 46c, and thus the fixed ring 47 does not come off from the spring collet 46, and so loss of the fixed ring 47 is prevented. In the above state, the spring collet 46 is fixed to the camera 16 via bolts 45, . . . (see FIG. 9C).

It is to be noted that when an image is captured using a digital camera, the auxiliary camera mount 44 (see FIG. 10A) having the bayonet grooves 44a, . . . can be used instead of the camera mount 15 described above.

Subsequently, as illustrated in FIG. 10A, the zoom housing 43 provided in the fourth bending part 12D is inserted into the inside of the spring collet 46 of the camera mount 15, and then the female screw 47b of the fixed ring 47 is screwed into the second male screw 46d of the spring collet 46. Consequently, the inner circumferential tapered surface 47a of the fixed ring 47 comes into contact with the outer circumferential tapered surface 46b of the spring collet 46, and thus the spring collet 46, which has reduced diameter because the slits 46a, . . . have been compressed, tightens the zoom housing 43, thereby integrally connecting the camera 16 and the borescope B as illustrated in FIG. 10B.

Thus completely prepared borescope B is inserted into the inside of the engine or transmission, and thus the objective lens unit 11 is made to face an object to be measured and an infrared image of the part is captured by the camera 16. The image obtained by the objective lens 23 is transmitted to the camera 16 via the first to third relay lenses 24A to 24C, the fourth to tenth relay lenses 34A to 34G, the first to fourth mirrors 27A to 27D, and the eyepiece lens 42, and thus even when the first to third lens barrels 14A to 14C of the borescope B each have a long dimension and are bent at the first to fourth bending parts 12A to 12D, an image of the object to be measured is captured without a hitch and the temperature of the object can be detected from the image.

Because the inside of the engine or transmission has a high temperature, the internal temperature of the borescope B inserted therein rises, the air in the first to third lens barrels 14A to 14C fluctuates, oil mist adheres to the outer surface of the objective lens 23, and thus the quality of the image captured by the camera 16 may deteriorate.

Figure 7:
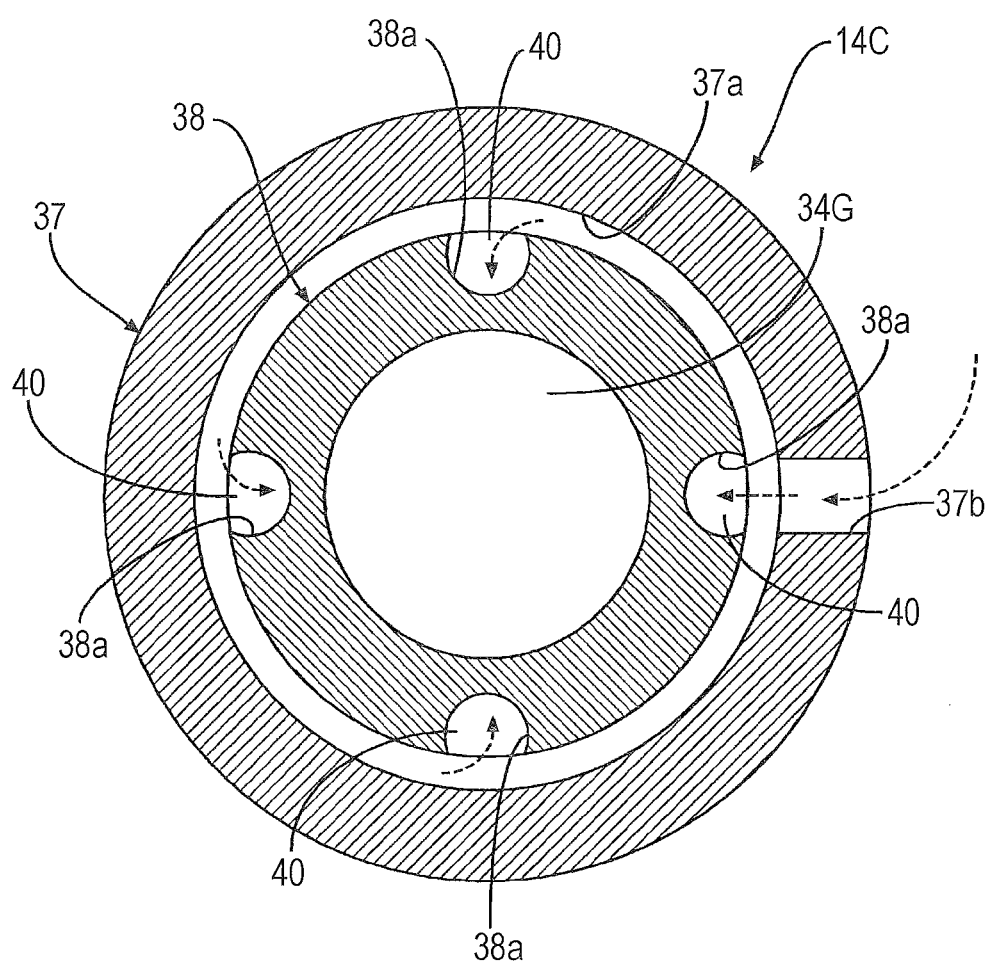
FIG. 7 is a cross-sectional view taken along line VII-VII of FIG. 6.

However, according to the present embodiment, the air, which has been supplied to the air supply hole 37b of the pipe member 37 from the air supply source 41, is supplied from the annular groove 37a of the pipe member 37 to the inside of the third lens barrel 14C through the air passages 40, . . . in the grooves 38a, . . . of the lens holder 38 (see FIGS. 6 and 7). In this manner, the air, which has been supplied to the inside of the third lens barrel 14C, flows forward through the air passages 36, . . . and the air holes 35c, . . . of respective outer circumferences of the six lens holders 35, . . . which are provided in the inside of the first to third lens barrels 14A to 14C, and the air is supplied to the objective lens unit 11. The inside of the objective lens unit 11 is provided with the four lens holders 22, . . . of the first to third relay lenses 24A to 24C and the objective lens 23, and the air, which has been supplied from the first lens barrel 14A, flows through the air passages 25, . . . and the air discharge hole 25' in the grooves 22a, . . . of each lens holder 22, and issues from the front end of the objective lens unit 11.

In this manner, the air, which has been supplied from the air supply source 41, flows through the inside of the borescope B and cools the inside, and thus fluctuation of air is prevented and the quality of the image captured by the camera 16 is assured. In addition, air issuing from the lens holder 22 of the objective lens 23 blows away oil mist or dust adhering to the front face of the objective lens 23, and thus more clear images can be obtained.

When an image is captured in a low temperature environment, the image quality may be reduced because condensation may occur at the objective lens 23, the first to third relay lenses 24A to 24C, the fourth to tenth relay lenses 34A to 34G, the eyepiece lens 42, and the first to third mirrors 27A to 27C. In this case, however, air warmed through the above-mentioned path may be supplied for heating, and thus deterioration of the image quality due to the condensation can be prevented.

Second Embodiment

Figure 11:
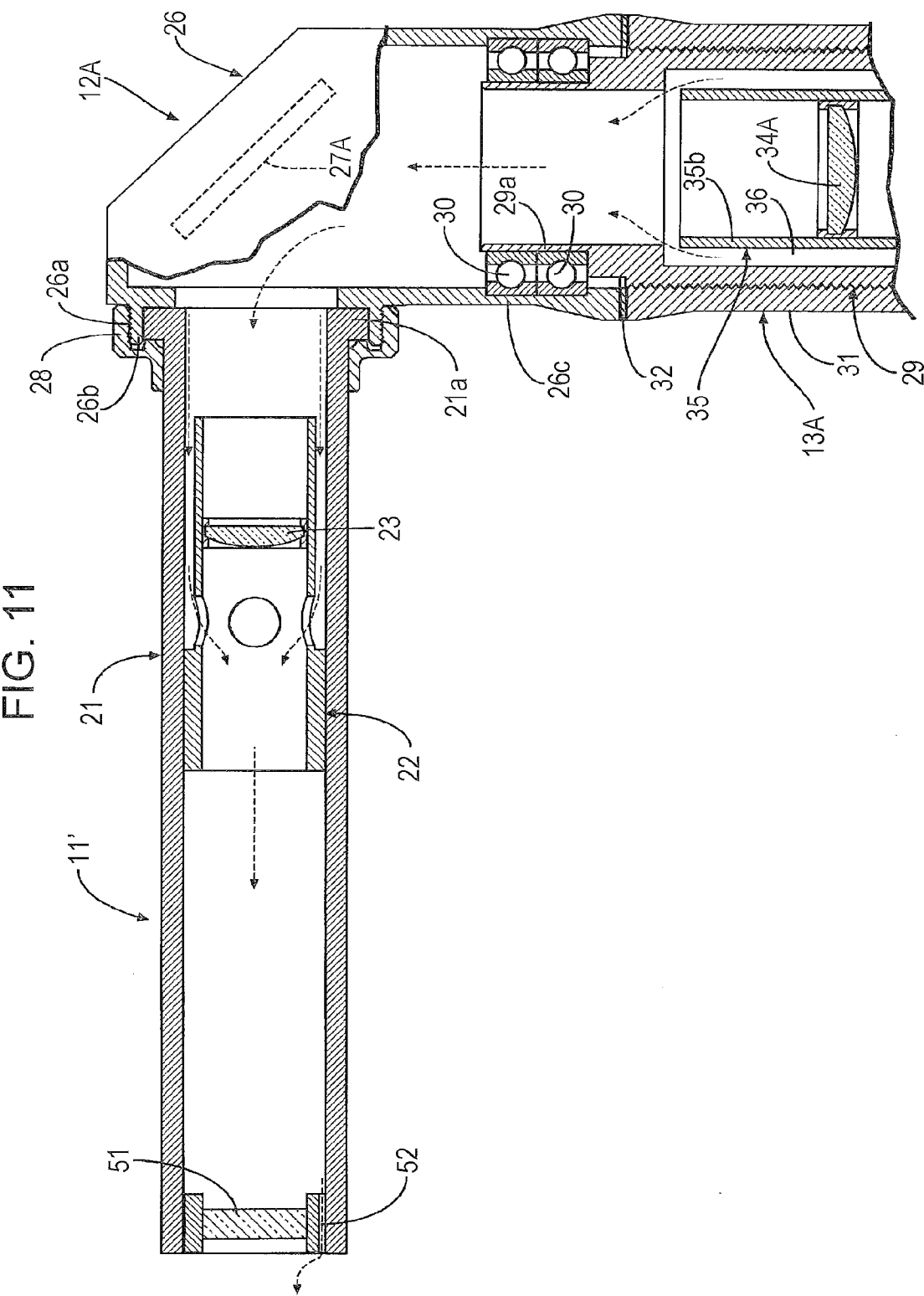
FIG. 11 is a view in a second embodiment, the view corresponding to FIG. 2.

Next, a second embodiment of the present disclosure will be described with reference to FIG. 11.

Although the object lens unit 11 in the first embodiment has a small diameter for a narrow area, an objective lens unit 11' in the second embodiment has a large diameter for a wide area. A transparent cover 51 is fixed to the front end of the pipe member 21, and the objective lens 23 is fixed via the lens holder 22 at an intermediate position of the pipe member 21. The object lens 23 and the lens holder 22 in the second embodiment are the same as the fourth to ninth relay lenses 34A to 34F and the lens holders 35, . . . in the first embodiment, and air can flow therethrough from rearward to forward. Air passages 52, . . . , through which air can flow from rearward to forward, are formed in the outer circumference of the cover 51 also.

The objective lens unit 11 in the first embodiment is configured such that an image is formed on the first mirror 27A in the first bending part 12A (see FIG. 1), and the objective lens unit 11' in the second embodiment is also configured such that an image is formed on the first mirror 27A in the first bending part 12A. In this manner, the image formation positions of exchangeable objective lens units 11, 11' are set to the same position, and thus lens focusing is not necessary each time different objective lens units 11, 11' are exchanged, thereby improving ease of operation.

It is to be noted that the image formation position of the objective lens units 11, 11' is not necessarily on the first mirror 27A in the first bending part 12A, and may be any position in the first bending part 12A or the first lens barrel 14A.

Third Embodiment

Figure 12:
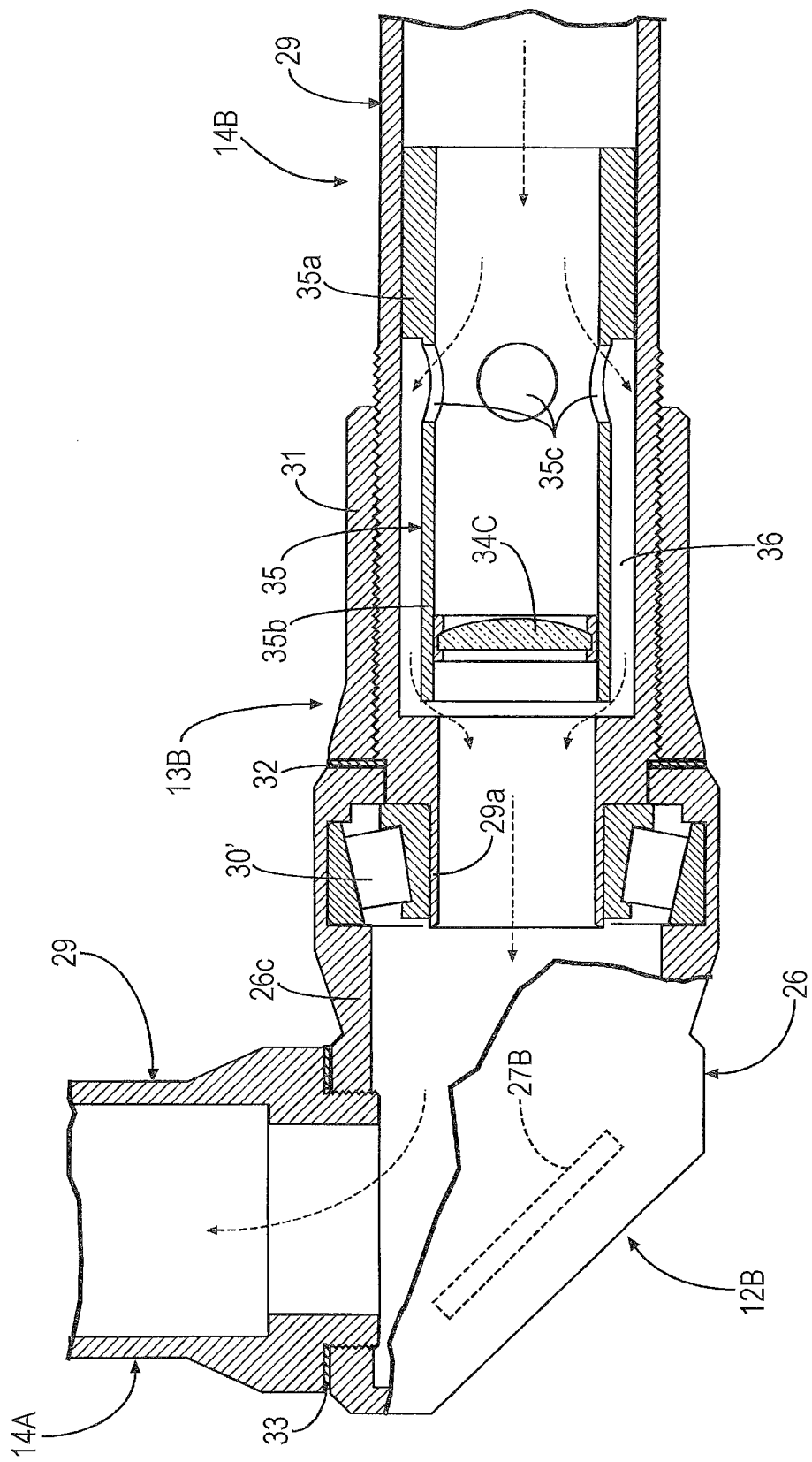
FIG. 12 is a view in a third embodiment, the view corresponding to FIG. 4.

Next, a third embodiment of the present disclosure will be described with reference to FIG. 12.

In the second joint part 13B in the first embodiment illustrated in FIG. 4, the inner cylindrical portion 29a of the pipe member 29 of the second lens barrel 14B and the outer cylindrical portion 26c of the housing 26 of the second bending part 12B are relatively rotatably connected via the two ball bearings 30, 30. However, in the third embodiment, the inner cylindrical portion 29a and the outer cylindrical portion 26c are relatively rotatably connected via a single roller bearing 30' (bearing).

The structure of the first joint part 13A and the third joint part 13C is also the same as the structure of the second joint part 13B described above. The third embodiment can also achieve the same operational effect as in the first embodiment.

Fourth Embodiment

Figure 13:
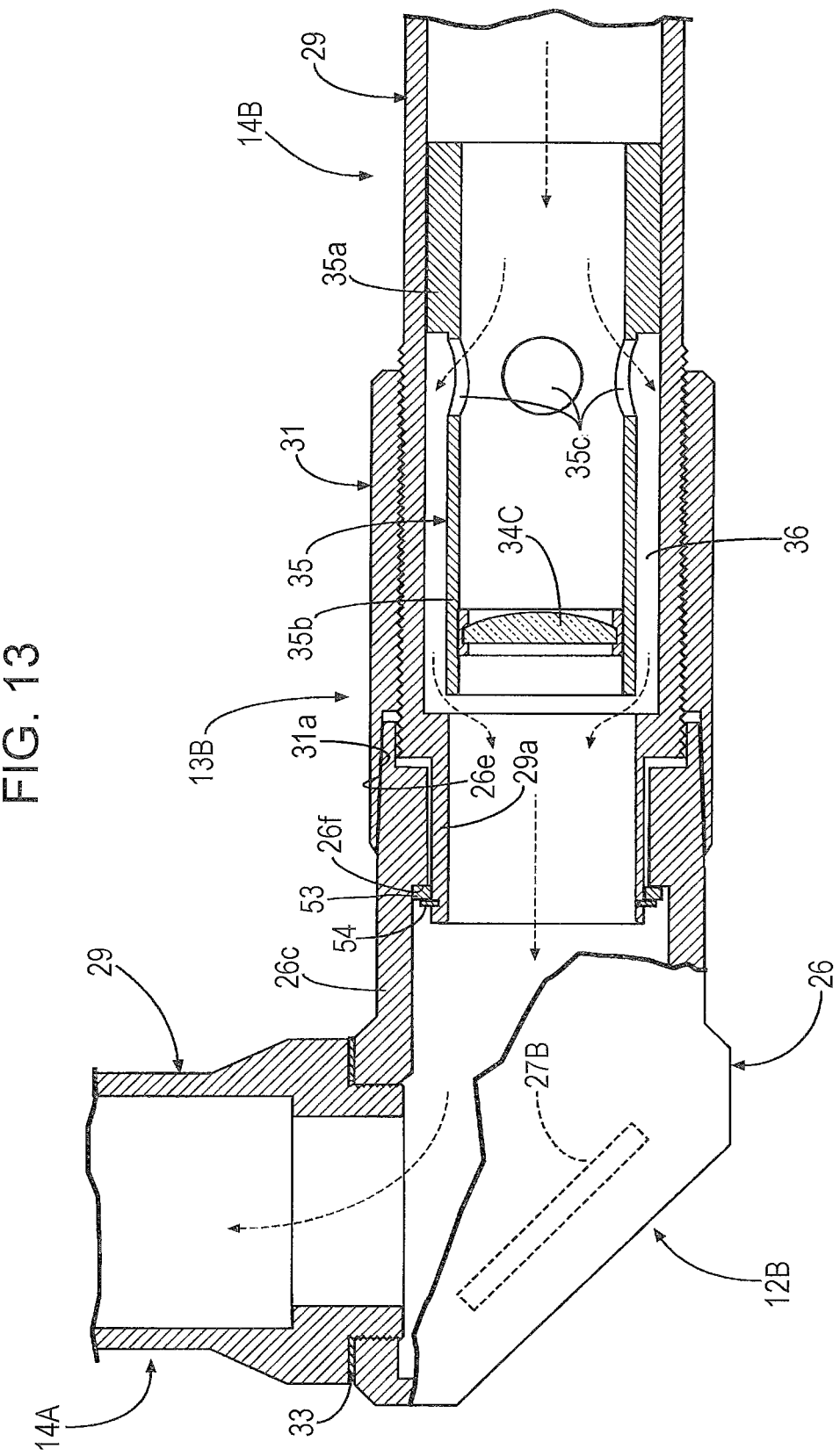
FIG. 13 is a view in a fourth embodiment, the view corresponding to FIG. 4.

Next, a fourth embodiment of the present disclosure will be described with reference to FIG. 13.

The outer cylindrical portion 26c of the housing 26 of the second bending part 12B includes an outer circumferential tapered surface 26e on the outer circumference at the rear end, and a step 26f on the inner circumference. An annular stopper 53, which faces the step 26f in a contactable manner, is fixed with a clip 54 to the front end of the inner cylindrical portion 29a of the pipe member 29 of the second lens barrel 14B, the inner cylindrical portion 29a being relatively rotatably fitted to the inner circumference of the outer cylindrical portion 26c. An inner circumferential tapered surface 31a, which may come into contact with the outer circumferential tapered surface 26e of the housing 26, is provided at the front end of the lock ring 31 which is screwed into the outer circumference of the pipe member 29.

Thus, in an unlocked state where the lock ring 31 is loosened and the outer circumferential tapered surface 26e and the inner circumferential tapered surface 31a are spaced apart, the second lens barrel 14B is rotated for a predetermined rotation angle relative to the second bending part 12B, and the lock ring 31 is tightened, so that the outer circumferential tapered surface 26e and the inner circumferential tapered surface 31a come into close contact with each other. Consequently, the stopper 53 comes into contact with the step 26f and the second bending part 12B and the second lens barrel 14B are integrally fixed to each other, and the second lens barrel 14B is automatically centered relative to the second bending part 12B.

In the above, the embodiments of the disclosure have been described, and various design modifications may be made without departing from the scope of the gist of the present disclosure.

For example, the numbers of the first to fourth bending parts 12A to 12D, the first to third joint parts 13A to 13C, and the first to third lens barrels 14A to 14C are not limited to those as described in each embodiment.

The application of the borescope B of the present disclosure is not limited to temperature measurement.

A prism may be used instead of the first to fourth mirrors 27A to 27D in the embodiments.

According to a first aspect of the embodiment, there is proposed a borescope including: a plurality of lens barrels which are connected via a plurality of bending parts each with a predetermined bend angle; a plurality of joint parts having changeable rotation angles of the bending parts relative to the lens barrels; an objective lens unit which has an objective lens and is detachably provided at a front end side of each of the lens barrels; a mirror or a prism disposed in each of the bending parts; a relay lens disposed in each of the lens barrels; and a camera mount provided at a rear end side of each of the lens barrels. Thus, the image captured by the objective lens is transmitted to an imaging device from forward to rearward through the relay lens provided in each lens barrel and the mirror or prism provided in each bending part in a bending manner. A path for transmitting an image can be changed in any manner. In contrast to the case where an objective lens with a long focal length, which causes a dark image, is used, brightness of the image can be assured. Furthermore, an objective lens can be exchanged with another objective lens unit having a different characteristic according to desired application.

According to a second aspect of the embodiment, there is proposed the borescope having the configuration of the first aspect, the borescope including an air supply hole which supplies air to an inside of each of the lens barrels; an air passage which communicates with a rear face side and a front face side of each of the relay lens; and an air discharge hole which communicates with a rear face side and a front face side of the objective lens, and allows air to be discharged to an outside of the objective lens unit. Thus, by cooling or heating the inside of the borescope to an appropriate temperature, not only deterioration of image quality can be prevented, but also foreign substances adhering to the objective lens can be blown away by air, so that dirt can be prevented, the deterioration of image quality being caused by disturbance of an image due to fluctuation of air in high temperature, or condensation of the relay lens, the lens, the mirror, and the prism.

According to a third aspect of the embodiment, there is proposed the borescope having the configuration of the first or second aspect, in which in each of the joint parts, an inner cylindrical portion provided in each of the lens barrels is rotatably fitted via a bearing to an inner circumference of an outer cylindrical portion provided in each of the bending parts, and a friction material is disposed between a lock ring and an end face of the outer cylindrical portion, the lock ring being screwed into an outer circumference of each of the lens barrels. Thus, not only the bending parts and the lens barrels can be relatively rotated smoothly so as to change the rotation angle, but also the fixed ring can be rotated, so that the friction material is compressed between the fixed ring and the end face of the outer cylindrical portion, and thus the bending parts and the lens barrels can be firmly fixed with a predetermined rotation angle.

According to a fourth aspect of the embodiment, there is proposed the borescope having the configuration of any one of the first to third aspects, in which the objective lens units are exchangeable, and an initial image formation position located rearwardly of the objective lens units is same. Thus, when an objective lens is exchanged with another objective lens unit having a different characteristic according to desired application, lens focusing is not necessary for each exchange, thereby improving ease of operation.

According to a fifth aspect of the embodiment, there is proposed the borescope having the configuration of any one of the first to fourth aspects, in which the camera mount includes a spring collet fixed to a camera and a fixed ring which is screwed into an outer circumference of the spring collet, the spring collet includes a plurality of slits which are open in a direction away from the camera and an outer circumferential tapered surface which is formed on each of the slits and has a larger diameter toward the camera, and the fixed ring includes an inner circumferential tapered surface which has a larger diameter toward the camera and is in contact with the outer circumferential tapered surface. Thus, when the fixed ring is tightened with the rear of the borescope being inserted into the spring collet, the spring collet reduces its diameter by the slit because the outer circumferential tapered surface is pressed against the inner circumferential tapered surface of the fixed ring, and thus the borescope and the camera can be easily connected.

According to a sixth aspect of the embodiment, there is proposed the borescope having the configuration of the fifth aspect, in which the camera mount includes a bayonet auxiliary camera mount for fixing another camera different from the camera. Thus, multiple types of cameras can be exchanged with each other easily, and thus convenience is improved.

Obviously, numerous modifications and variations of the present invention are possible in light of the above teachings. It is therefore to be understood that within the scope of the appended claims, the invention may be practiced otherwise than as specifically described herein.

What is claimed is:

1. A borescope comprising:
   a plurality of bending parts with predetermined bend angles;
   a plurality of lens barrels which are connected via and between respective ones of the plurality of bending parts;
   a plurality of joint parts via which rotation angles of the plurality of bending parts is changeable relative to the plurality of lens barrels, each of the plurality of joint parts having a lock ring disposed around an outer circumference of one of the plurality of lens barrels and configured to be selectively tightened to apply a frictional force and loosened to relieve the frictional force by rotating the lock ring relative to one of the plurality of lens barrels thereby moving the lock ring between a tightened position adjacent to one of the plurality of bending parts and a loosened position spaced from the one of the plurality of bending parts;
   an objective lens device which has an objective lens and is detachably provided at a front end side of the plurality of lens barrels;
   a plurality of reflectors respectively disposed in the plurality of bending parts;
   a plurality of relay lenses respectively disposed in the plurality of lens barrels; and
   a camera mount provided at a rear end side of the plurality of lens barrels.

2. The borescope according to claim 1, further comprising:
   an air supply hole through which air is to be supplied to an inside of each of the plurality of lens barrels;
   a plurality of air passages which each communicate with a rear face side and a front face side of each of the plurality of relay lenses; and
   an air discharge hole which communicates with a rear face side and a front face side of the objective lens and through which air is to be discharged to an outside of the objective lens device.

3. The borescope according to claim 1,
   wherein in each of the plurality of joint parts, an inner cylindrical portion provided in each of the plurality of lens barrels is rotatably fitted via a bearing to an inner circumference of an outer cylindrical portion provided in each of the plurality of bending parts, and a friction material is disposed between the lock ring and an end face of the outer cylindrical portion, the lock ring being screwed into the outer circumference of each of the plurality of lens barrels.

4. The borescope according to claim 1,
   wherein the objective lens device is exchangeable to another objective lens device different from the objective lens device, and
   wherein an initial image formation position located rearward of the objective lens unit is same as an initial image formation position located rearward of the another objective lens unit.

5. The borescope according to claim 1,
   wherein the camera mount includes
      a spring collet provided to be fixed to a camera, and
      a fixed ring which is screwed into an outer circumference of the spring collet,
   wherein the spring collet includes
      a plurality of slits which are open in a direction away from the camera, and
      an outer circumferential tapered surface which is formed on each of the plurality of slits and has a diameter gradually increasing toward the camera, and
   wherein the fixed ring includes an inner circumferential tapered surface which has a diameter gradually increasing toward the camera and which is in contact with the outer circumferential tapered surface.

6. The borescope according to claim 5,
   wherein the camera mount includes a bayonet auxiliary camera mount to fix another camera different from the camera.

7. The borescope according to claim 1,
   wherein each of the plurality of reflectors comprises one of a mirror and a prism.

8. The borescope according to claim 1,
   wherein each of the plurality of joint parts comprises a joint.

9. The borescope according to claim 1,
   wherein the plurality of joint parts each include a bearing configured to allow the plurality of bending parts to rotate relative to the plurality of lens barrels.

10. The borescope according to claim 1,
    wherein the plurality of bending parts are each rotatable in respective planes that are substantially orthogonal to corresponding planes in which the predetermined bend angles lie.

11. The borescope according to claim 1,
    wherein the plurality of bending parts are rotatable relative to the plurality of lens barrels such that any rotational angle can be formed between the plurality of bending parts and the plurality of lens barrels.

12. The borescope according to claim 1,
    wherein a first one of the plurality of bending parts is rotatable relative to a second one of the plurality of bending parts.

13. The borescope according to claim 1, wherein loosening the lock ring to relieve the frictional force allows rotation of the plurality of the bending parts relative to the plurality of lens barrels when the lock ring is in the loosened position, and tightening the lock ring to apply the frictional force integrates the plurality of joint parts and the plurality of lens barrels when the lock ring is in the tightened position.

14. The borescope according to claim 1, wherein the objective lens device is detachable from the front end side of the plurality of lens barrels.

15. The borescope according to claim 1,
    wherein one of the lock rings is disposed around the outer circumference of a first lens barrel of the plurality of lens barrels, the first lens barrel being connected to a first bending part of the plurality of bending parts, and wherein the first bending part remains connected to the first lens barrel when the one of the lock rings disposed on the outer circumference of the first lens barrel is moved to the loosened position spaced away from the first bending part.

16. A borescope comprising:
a first bending part having a first reflector;
a second bending part having a second reflector;
a first lens barrel connected to and disposed between the first bending part and the second bending part;
a first joint part configured to allow rotation of the first lens barrel with respect to one of the first bending part and the second bending part, the first joint part having a lock ring disposed on an outer circumference of the first lens barrel and configured to be selectively tightened to apply a frictional force and loosened to relieve the frictional force by rotating the lock ring relative to the first lens barrel thereby moving the lock ring between a tightened position adjacent to one of the first bending part and the second bending part and a loosened position spaced from the one of the first bending part and the second bending part; and
a plurality of relay lenses disposed in the first lens barrel,
wherein the first bending part is connected to:
an objective lens device having an objective lens, the objective lens device being detachably attached to the first bending part; or
a camera mount, and wherein the first and second bending parts are bent at respective predetermined bend angles.

17. The borescope according to claim 16, further comprising:
a second lens barrel connected to the second bending part; and
a third bending part having a third reflector and being connected to the second lens barrel.

18. The borescope according to claim 17, further comprising:
a third lens barrel connected to the third bending part;
a fourth bending part having a fourth reflector and being connected to the third lens barrel,
wherein the camera mount is provided at the first bending part and the objective lens device is provided at the fourth bending part.

19. The borescope according to claim 16,
wherein the lock ring is disposed adjacent to the first bending part when moved to the tightened position, and
wherein the first bending part remains connected to the first lens barrel when the lock ring disposed on the outer circumference of the first lens barrel is moved to the loosened position spaced away from the first bending part.

* * * * *